United States Patent [19]

Chao

[11] 4,394,316
[45] Jul. 19, 1983

[54] COPPER MODIFIED MANCOZEB

[75] Inventor: Yen-Yau H. Chao, North Wales, Pa.

[73] Assignee: Rohm and Haas Company, Philadelphia, Pa.

[21] Appl. No.: 186,060

[22] Filed: Sep. 11, 1980

[51] Int. Cl.³ .......................... C07F 13/00; C07F 1/08
[52] U.S. Cl. ................................. 260/429 K; 424/286
[58] Field of Search ..................... 260/429 K; 424/286

[56] References Cited

U.S. PATENT DOCUMENTS

| | | | |
|---|---|---|---|
| 2,848,297 | 8/1958 | Hill | 260/429 R X |
| 3,082,229 | 3/1963 | Nash | 260/429 K |
| 3,210,394 | 10/1965 | Nemec et al. | 260/429 K |
| 3,259,643 | 7/1966 | Nash | 260/429 R |
| 3,379,610 | 4/1968 | Lyon et al. | 424/286 |
| 3,499,018 | 3/1970 | Stevenson | 424/286 X |
| 3,523,960 | 8/1970 | Lehureau | 260/429 K |
| 4,217,293 | 8/1980 | Adams | 260/429 K |

FOREIGN PATENT DOCUMENTS 660165 7/1966 South Africa .
996264 6/1965 United Kingdom .

OTHER PUBLICATIONS

S. Lesage, "Reduction of the Formation of Ethylenethiourea from Ethylenebis(dithiocarbamates) by $Cu^{2+}$", J. Agric. Food Chem., 1980, 28, 787–790.

E. R. Brocker & C. Schlatter, "Influence of Some Cations on the Intestinal Absorption of Maneb", J. Agric. Food Chem., 1979, 27, 303–306.

"Water Stable Maneb–Zinc–Copper Oxychloride Fungicide", Chem. Abstracts, 90224, 1969, 71, 254.

"Fungicide Formulations for Agricultural Use", Chem. Abstracts, 69663, 1969, 71, 219.

"Ethylenebis(dithiocarbamate) Mixed Salts", Chem. Abstracts, 3324g, 1969, 70.

"Fungicide Compositions", Chem. Abstracts, 85624p, 1976, 84.

"Ternary Fungicide Compns. Contg. Mn Ethylene Bis Dithiocarbamate", Derwent No. 2189H/00, (1967).

"Fungicidal Plant Protection Compositions Containing Cu Salts", Derwent No. 30261-H/00, (1966).

"Manganese Ethylene Bis–Dithiocarbamate Complex Fungicide", Derwent No. 3067H/00, (1967).

"Fungicidal Composition Containing Cu As a Basic Salt . . . ", Derwent No. 6434H/00, (1968).

"Copper Carboxylate Carbamate Algicide Fungicide", Derwent No. 12215X/07, (1974).

"Fungicidal Compn.–Maneb/Cu Compound/Zn Salt", Derwent No. 2998H/00, (1967).

"Dithiocarbamate Fungicides Improved By Adding Cu", Derwent No. 2994H/00, (1964).

*Primary Examiner*—Helen M. S. Sneed
*Attorney, Agent, or Firm*—Alex R. Sluzas

[57] ABSTRACT

This invention relates to copper modified mancozeb (the reaction product of manganese ethylene-bis-dithiocarbamate and soluble zinc (II) ion) and processes for preparing same which produces a product which reduces the generation of ethylene thiourea on long term storage of the product, reduces the solubilized ethylene thiourea produced during the manufacture or storage of mancozeb, maintains or increases the fungicidal activity of mancozeb, and is more persistent in the field.

5 Claims, No Drawings

COPPER MODIFIED MANCOZEB

BACKGROUND OF THE INVENTION

Numerous ethylene-bis-dithiocarbamate products exist which have proven commercial value as protective fungicides. The more commercially important of these include nabam, zineb, maneb and mancozeb. All of these products contain varying amounts of ethylene thiourea which is produced during the manufacturing process and on long term storage. Various processes for stabilizing these products have been developed over the years with mixed success. Such stabilization processes have included the addition of hexamethylene tetramine or paraformaldehyde and/or various washes to remove the impurity at various steps in the manufacturing process. U.S. Pat. No. 3,379,610 granted Apr. 23, 1968 discloses a mixed manganese, zinc, cobalt metal salt complex of ethylene-bis-dithiocarbamic acid but does not specifically disclose the copper modified mancozeb of the present invention nor does it recognize the unique ability of the product of this invention to chemically stabilize ethylene-bis-dithiocarbamic acid. The *Journal of Agriculture and Food Chemistry*, Vol. 28, 787–790 (1980) discloses that soluble copper(II) ion stabilizes maneb and decreases the formation of ethylene thiourea to trace amounts when high weight ratios of copper sulfate to maneb (ten fold excess) are utilized. Various combinations of mancozeb with insoluble copper salts such as copper oxychloride, copper hydroxide, copper carbonates and basic copper sulfates are known. The South Africa Pat. No. 660,165 published July 15, 1966 discloses products formed from the reaction of ethylene-bis-dithiocarbamate sodium salt with mixtures of copper, manganese and zinc sulfates wherein the ratio of copper:manganese:zinc is 1.07:1.22:1.79.

SUMMARY OF THE INVENTION

This invention relates to a copper modified mancozeb (the reaction product of manganese ethylene-bis-dithiocarbamate and soluble zinc (II) ion) and processes for preparing same which produces a product which reduces the generation of ethylene thiourea in long term storage of the product, reduces the solubilized ethylene thiourea produced during the manufacture or storage of mancozeb, maintains or increases the fungicidal activity of mancozeb, is more persistent in the field and thus is useful as a protective fungicide for controlling phytopathogenic fungi.

Ethylene thiourea is a decomposition product of ethylenebisdithiocarbamic acid. Because of its suspected carcinogenecity various means have been sought to control or lower the amount of ethylene thiourea in the various metal salts of ethylene-bis-dithiocarbamate. The products available through the process of this invention not only release substantially less ethylene thiourea upon contact with water at room or elevated temperatures over different lengths of time, but also remove, to various extents, the existing, solubilized ethylene thiourea in the aqueous solutions. The new product of this invention is also safe on agronomic crops and is effective in controlling phytopathogenic fungi at low rates of application.

To prepare the product of this invention, an aqueous solution of mancozeb is reacted with a water solubilized copper (II) ion. The anions which can be utilized to satisfy the valence of the copper (II) ion can be any anion that can be made to release the copper (II) ion. Such anions include halide, nitrate, perchlorate, sulfate, chlorate and bromate. Ammonia and lower alkylamine complexes can also be utilized to provide the source of copper (II) ion.

The copper modified mancozeb of this invention contains from about 2.5% to about 20% copper (II) ion, preferably from about 3% to about 10% copper (II) ion, more preferably from about 4% to 8% copper (II) ion.

According to the process of this invention, the copper (II) ion is taken up, reacted with, or complexed by mancozeb to form the copper modified mancozeb of this invention. The reaction proceeds quite readily between 1 minute and 2 hours at from about 5° to about 90° C. The product may be isolated from the mixture by filtering, washing, then drying or spray drying, centrifuging and the like. Below the decomposition temperature the entire reaction mixture can be dried together with the soluble salts in the product, or the product may be washed before drying.

Because of the fast reaction between the copper (II) and mancozeb in water, the product may also be prepared as a dry blend of a copper (II) salt which can be water solubilized with mancozeb. Such a dry mixture will be readily converted into the product of this invention when contacted with water.

The product may be dried by spray drying, vacuum drying or tray drying. After the product has been dried, it may be ground, micropulverized, micronized or crushed, to make the product more finely divided.

A dispersing agent, such as sodium lignin sulfonate, sodium naphthalene-formaldehyde sulfonate, or sodium dioctylsulfosuccinate, and/or a stabilizing agent, such as hexamethylenetetramine may be added to the slurry to be dried or to the dried product.

Typical preparations of reaction products of this invention are presented by the following examples. These examples are illustrative of how to prepare the product of this invention and are not to be interpreted as limitations on the breadth and scope thereof. Parts are by weight unless otherwise designated. These samples were analyzed by electron spectrocopy for chemical analysis (ESCA) utilizing a Du Pont 650 electron spectrometer and by atomic absorption (AA) utilizing a Perkin Elmer Model 5000 spectrophotometer.

In the ESCA analysis, the following procedure was utilized. The sample was ground to a powder and placed with a double faced adhesive onto a metal holder with a ¼ inch diameter sample compartment. Soft x-ray (mainly K-alpha line from magnesium) bombards the whole area and signal intensity is measured at $2P^{3/2}$ shell binding energy of each metal. The metals analyzed for were zinc (1021 ev.), copper (931 ev.), cobalt (779 ev.) and manganese (641 ev.).

In the AA analysis standard procedures known in the art were followed. The metals analyzed for were copper (324.7 nm), manganese (279.5 nm), cobalt (240.7 nm) and zinc (213.9 nm).

EXAMPLE 1

To an agitated slurry of 300 parts of a commercial mancozeb and 500 parts of water were added 30 parts of anhydrous copper (II) sulfate and 170 parts of water. After an hour at room temperature, the mixture was dried at 40°–60° C. under reduced pressure. The dried product was then micronized with a Micro-Mill TM.

ESCA studies show that the product is not a simple mixture of copper salt and mancozeb.

EXAMPLE 2

A commercial mancozeb (100 parts) was dry-blended with 10 parts anhydrous copper (II) sulfate. ESCA studies show that within the contact time of one to two minutes with water, a substantial amount of copper is taken up, reacted with, or complexed by mancozeb.

The copper modified mancozeb of this invention has the unique ability to remove, to various extents, solubilized ethylene thiourea in aqueous solutions. The data in Table I clearly demonstrates this unique ability.

TABLE I
THE REMOVAL OF THE SOLUBILIZED
ETHYLENE THIOUREA (ETU) IN WATER
BY THE COPPER MODIFIED MANCOZEB

| Aqueous Sample Before Modification | Modification | % ETU in Water per 100% Solid Fungicide |
|---|---|---|
| mancozeb HC-8[a] | before CuSO4 addition | 0.11 |
| mancozeb HC-8[b] | after CuSO4 addition | 0.001 |
| mancozeb HC-34[c] | before CuSO4 addition | 0.25 |
| mancozeb HC-34[d] | after CuSO4 addition | 0.02 |

[a]Composition - 1 part mancozeb + 3 parts water dried on a rotary evaporator and diluted to 0.5%
[b]Composition - 1 part mancozeb + 10% by weight CuSO4 + 3 parts water dried on a rotary evaporator and diluted to 0.5% in water
[c]Composition - 1% aqueous mancozeb + equal volume of water.
[d]Composition - 1% aqueous mancozeb + equal volume of 0.1% CuSO4.

It is known that cupric ethylene-bis-dithiocarbamate (Barratt and Horsfall, 1947, Lesage, 1980) is extremely insoluble, very stable and has low fungicidal activity. The extra stability of cupric EBDC makes the degradation of the product very slow, thus generating less ETU. The low fungicidal activity makes it impractical to use this product as a commercial fungicide. However, the mechanism by which the product of this invention controls.

ETU formation (Table I) is unrelated to the stability of the dithiocarbamate. The copper modified mancozeb of this invention will remove, to various extents, the solubilized ETU in the spray tank.

Another feature of the product of this invention is its ability to suppress the release of ETU when the product is subjected to boiling water. The copper (II) modified mancozeb (of this invention) generates much less ETU than the copper (II) modified maneb (manganese salt of ethylene-bis-dithiocarbamate). The following experiment was designed to demonstrate this phenomenon.

In this experiment samples from three different batches of mancozeb (HC-331, II & III) and two different batches of maneb (HC-33 IV & V) were used to demonstrate the general applicability of the present invention. Samples from each of these batches were diluted to 0.5% in water and placed in boiling water for ten minutes. These samples were then analyzed for the percent ETU based on the percent solid product present. Subsequently, samples from these same batches were diluted to 0.5% in water and treated with 0.05% CuSO4, then placed in boiling water for ten minutes. These copper modified samples were analyzed for the percent ETU present based on the percent solid product. The results of these tests are given below.

TABLE II
THE GENERATION OF ETU FROM THE AQUEOUS
SOLUTIONS OF THE COPPER (II)
MODIFIED MANCOZEB AND THE COPPER (II)
SALT OF MANEB IN BOILING WATER
BATH FOR TEN MINUTES.*

| Sample | ETU/Product Solids (%) |
|---|---|
| HC-33 (I) mancozeb | 6.57 |
| Cu (II) modified HC-33 (I) | 0.82 |
| HC-33 (II) mancozeb | 7.09 |
| Cu (II) modified HC-33 (II) | 0.80 |
| HC (III) mancozeb | 6.32 |
| Cu (II) modified HC-33 (III) | 1.95 |
| HC-33 (IV) maneb | 6.74 |
| Cu (II) modified HC-33 (IV) | 3.33 |
| HC-33 (V) maneb | 5.29 |
| Cu (II) modified HC-33 (V) | 2.71 |

*The amount of ETU before heating is usually very small (<10%) in comparison with that after heating.

The use of water solubilized copper (II) ion in the product of this invention is very crucial. When mancozeb was combined with the insoluble copper (II) salts, such as copper oxychloride, copper tribasic sulfate, copper hydroxide, Bordeaux mixture, or copper fatty acid-copper rosin acid, even up to 1:1 ratios, none of the products obtained reduced as much solubilized ETU in the spray tank as the copper modified mancozeb of the present invention which uses substantially less but soluble copper (II) ion.

The following test was performed to demonstrate the stability of the copper modified mancozeb. In this test mancozeb and a copper modified (treatment with 10% CuSO4 by weight based on mancozeb ≈4% Cu(II) ion) mancozeb are subjected to heat treatment by placing vials containing aqueous suspensions in boiling water for 10 minutes. This study also employed ethylenediaminetetracetic acid (EDTA) at pH 11 to solubilize the mancozeb and copper modified mancozeb for purpose of analyses. The results of this test are presented in Table III below.

TABLE III
THE STABILITY OF COPPER MODIFIED MANCOZEB
IN THE BOILING TEST

| | Solution contains 4% Cu (II) | Sample Vial in boiling water for 10 minutes | EDTA pH 11 | % ETU[b]/Solids |
|---|---|---|---|---|
| I | − | − | − | 0.24 |
| II | + | − | − | 0.02 |
| III | − | − | + | ~ 0.5 (t = ?) |
| IV | + | − | + | ~ 0.8[a] (t = ?) |
| V | − | + | − | 3.5 |
| VI | + | + | − | 0.7 |
| VII | − | + | + | 5.2 |
| VIII | + | + | + | 0.7 |

[a]It took rather long time (>20 min.) to dissolve the Cu (II) modified mancozeb with EDTA, so the ETU value thus determined should be viewed with reservation.
[b]ETU is determined by extraction with water.

The following test which was performed utilizing the test procedures given in Table III above demonstrates that copper modified mancozeb is unexpectedly more stable than the corresponding copper treated maneb or zineb as shown by the high levels of ETU obtained with the copper treated maneb and zineb in the heat treatment test.

TABLE IV

THE EFFECT OF Cu (II) ON OTHER EBDC's

| | Sample vial | | |
|---|---|---|---|
| | 4% Cu (II) | In boiling water 10 Min. | % ETU/Solids |
| maneb | − | − | 1.0 |
| maneb | + | − | 0.2 |
| maneb | − | + | 4.15 |
| maneb | + | + | 3.76 |
| zineb | − | − | 0.6 |
| zineb | + | − | 0.2 |
| zineb | − | + | 4.11 |
| zineb | + | + | 2.89 |

The following Table V demonstrates the lower limit at which the dilute solutions of 2% and 4% copper modified mancozeb is stable.

TABLE V

THE EFFECT OF Cu (II) ON DILUTE MANCOZEB SOLUTIONS

| Concentration Mancozeb | % Cu (II) :mancozeb | Heating Time at 38° C. | % ETU/Solids |
|---|---|---|---|
| 0.5% | 0.0% | 0 hr. | 0.21 |
| | | 2 hrs. | 0.34 |
| 0.5% | 2% | 0 hr. | 0.06 |
| | | 2 hrs. | 0.28 |
| 0.5% | 4% | 0 hr. | 0.03 |
| | | 2 hrs. | 0.06 |

Table VI below demonstrates the effect of copper levels on ETU formation in the boiling water test.

TABLE VI

| % Cu (II) ion | % ETU/mancozeb |
|---|---|
| 0 | 7.1 |
| 0.8 | 6.1 |
| 4 | 1.8 |
| 8 | 0.8 |
| 20 | 0.5 |
| 40 | 0.2 |

The following test demonstrates the unexpected superiority of the copper modified mancozeb as compared to cobalt modified mancozeb in its ability to remove ETU from solution at room temperature.

TABLE VII

THE CONTROL OF ETU BY Co (II) and Cu (II) MODIFIED MANCOZEB

| | | % ETU based on mancozeb | | | |
|---|---|---|---|---|---|
| | No Metal Added | 4% Cu (II) | 8% Cu (II) | 4% Co (II) | 8% Co (II) |
| Before Heat Treatment | 0.17 | 0.04 | — | 0.19 | — |
| After Heat Treatment | 7.2 | 2.6 | 0.51 | 0.9 | 0.7 |

The copper modified mancozeb of this invention is a broad-spectrum fungicide which possesses a high degree of activity against assorted phytopathogenic fungi. This product is particularly effective at rates of application from about 50 to about 2000 ppm in controlling phytopathogenic fungi such as barley net blotch (*Helminthosporium teres*) on barley plants, cucumber anthracnose (*Colletotrichum lagenarium*) on cucumber, bean powdery mildew (*Erysiphe polygoni*) on bean plants, grape downy mildew (*Plasmopora viticola*) on grape seedlings, rice blast (*Piricularia oryzae*) on rice plants, tomato late blight (*Phytophthora infestans*) on tomato seedlings, and wheat stem rust (*Puccinia graminis* f. sp. *tritici* race 15B-2) on wheat seedlings.

In evaluating this product, a preliminary fungicidal evaluation is carried out by applying the product at an application rate of 300 ppm and spraying the plants to run off in a carrier volume of about 150 gallons/acre.

The general procedure is to take potted plants in proper condition of growth for susceptibility to the fungal disease to be evaluated, to spray these plants on a moving belt with the product to be evaluated and allow them to dry. The proper plants are then inoculated with the fungal spores and then allowed to incubate until the disease has developed and then percent control is read or estimated.

The following test methods are employed in evaluating the fungicidal activity of the product of this invention.

EXAMPLE A—Barley Net Blotch (*Helminthosporium teres*)

Barley plants (var. Wong) are trimmed to a height of approximately 2.5 inches, 24 hours prior to chemical application. This procedure provides plants of a uniform height and permits rapid inoculation of treated plants. The barley plants are inoculated by spraying the foliage of the plants with a hand sprayer until small droplets of the inoculum are observed on the leaves. Inoculated plants are incubated in a humid environment at 75°-80° F. for 24 hours prior to being placed in the greenhouse at 70°-75° F. Treatment comparisons are made 6 to 7 days after inoculation. Typical barley net blotch symptoms initially appear as irregular sunken water-soaked areas which become necrotic as the lesions enlarge.

EXAMPLE B—Cucumber Anthracnose (*Colletotrichum lagenarium*)

Cucumber (var. 'Marketer') seedlings are 14 days old when treated.

*Colletotrichum lagenarium* is cultured on green bean agar (GBA) in petri plates for 7 days under dark conditions. Petri plates of GBA are inoculated with 0.5 ml. of a spore suspension prepared in sterile water. The spore suspension is subsequently spread over the surface of the GBA plate by means of a sterile glass rod bent in the form of a hockey stick. Spores are harvested from plates by adding deionized water to the GBA plates. The agar surface is scraped with a rubber policeman or similar blunt object. The spore suspension is filtered through cheesecloth to remove mycelial and agar fragments and then adjusted to a concentration of $1-2 \times 10^5$ spores per ml.

Treated cucumber plants are inoculated by spraying the leaves (especially the underside) until a uniform film of inoculum is observed on the plant. Inoculated plants are incubated in a humid environment at 70°-75° F. for 72 hours. They are removed from the humid environment, allowed to dry, and placed under existing greenhouse conditions.

Treatment comparisons are made 10-14 days after inoculation. Typical anthracnose symptoms are small spots on the foliage that begin as small yellowish or water-soaked areas that enlarge rapidly and become necrotic.

EXAMPLE C—Bean Powdery Mildew (*Erysiphe polygoni*)

Bean plants (var. Dwarf Hort) are thinned to two plants per pot 24 hours prior to chemical application. Bean plants are inoculated by spraying the leaves and stems with inoculum until a uniform film of inoculum is observed on the plant. Inoculated plants are maintained under existing greenhouse conditions. Treatment comparisons are made 8 to 10 days after inoculation. Typical bean powdery mildew symptoms are circular white mycelial mats (fructifications) on the leaf surface.

EXAMPLE D—Grape Downy Mildew *Plasmopora viticola*)

Grape seedlings (var. Siebel 1000) 4 to 5 inches tall are used. *Plasmopora viticola* is cultured on grape leaves for 7 days at 65°–75° F. The grape plants are inoculated by spraying the leaves with a hand held air brush until small uniform droplets of inoculum are observed on the leaves. The inoculated plants are incubated in a humid environment at 65°–70° F. for 48 hours prior to being placed in a growth room. Typical grape downy mildew symptoms appear on the upper surface as pale-yellow spots variable in size and form, frequently circular without a distinct line of demarcation. Under humid conditions the lower leaf surface is covered by conspicuous fungal growth.

EXAMPLE E—Rice Blast (*Piricularia oryzae*)

Rice plants (var. Nova 66) are trimmed to a height of approximately 5 inches, 24 hours prior to chemical application. This procedure provides plants of uniform height and permits rapid inoculation of treated plants. Rice plants are inoculated by spraying the leaves and stems with an air brush until a uniform film of inoculum is observed on the leaves. The inoculated plants are incubated in a humid environment (75°–85° F.) for 24 hours prior to being placed in a greenhouse environment. Treatment comparisons are made 7 to 8 days after inoculation. Initial rice blast lesions appear as small brown necrotic spots on the foliage. The typical lesion is eliptical, 1 to 2 cm. long with a large necrotic gray center and brown margins.

EXAMPLE F—Tomato Late Blight (*Phytophthora infestans*)

Tomato (var. Rutgers) seedlings, 2.5 to 3 inches tall, are fertilized with a water soluble fertilizer 4 to 5 days prior to chemical application to promote rapid succulent growth and better symptom expression. The spore suspension is applied with a DeVilbiss atomizer at 8 to 10 psi. air pressure onto the leaf undersurface until fine droplets are formed. Inoculated seedlings are placed in a humid environment at 60°–62° F. for 40 to 45 hours, prior to being placed in the greenhouse at 70°–75° F. Treatment comparisons are made 5 to 6 days after inoculation. Initially, typical tomato late blight symptoms appear as irregular, greenish-black, water-soaked patches which enlarge and become brown, with a firm corrugated surface. Severe infection will resemble frost damage.

EXAMPLE G—Wheat Stem Rust (*Puccinia graminis* f. sp. *tritici* race 15B-2)

Seven-day-old wheat plants (var. Monon) are trimmed to approximately 2.5 inches, 24 hours prior to chemical application to provide a uniform plant height and to facilitate uniform inoculation. Wheat stem rust is cultured on wheat seedlings (var. Monon) for a period of 14 days under existing greenhouse conditions. Wheat plants are inoculated by applying the stem rust spore suspension, until run-off, with a DeVilbiss atomizer at 5 psi. air pressure. After inoculation, the plants are placed into a humid environment at approximately 68° F. A timer is used to permit 12 hours of continuous darkness followed by a minimum of 3 to 4 hours of light with an intensity of 500 foot candles. The temperature in the chamber should not exceed 85° F. At the end of the light period, the fogger is turned off and vented to allow the plants to dry slowly prior to being placed into a greenhouse environment. The plants are permitted to grow under greenhouse conditions for a period of 2 weeks prior to making treatment comparisons. Wheat stem rust is characterized by brick red spores in irregularly shaped sori on the leaves and stems of the wheat seedlings.

Table III below demonstrates the activity of the copper modified mancozeb of the present modified invention as compared to the unmodified mancozeb. As can be seen, the copper modified mancozeb of the present invention is unexpectedly equivalent to or better than the unmodified mancozeb, since it is known in the art that copper EBDC is far less soluble than mancozeb and thus less efficacious on a pound per pound basis.

TABLE VIII

IN VIVO ACTIVITY OF MANCOZEB AND MANCOZEB + CuSO$_4$ (10%) AGAINST SELECTED FOLIAR PLANT PATHOGENS

| Compound | Conc. (ppm ai) | Disease Control Rating[1] | | | | | | |
|---|---|---|---|---|---|---|---|---|
| | | BH[2] | RB | CA | BPM | GDM | TLB | WSR |
| Mancozeb[3] | 1200 | A | A | A | D | A | A | B |
| CuSO$_4$ (10%) | 600 | A | A | A | D | A | A | B |
| | 300 | A | B | A | E | B | A | E |
| | 150 | A | A | C | E | E | C | E |
| | 75 | C | C | A | E | E | E | E |
| | 38 | E | E | E | E | E | E | E |
| Mancozeb | 1200 | A | A | B | E | A | A | B |
| | 600 | A | A | A | E | A | B | B |
| | 300 | B | B | A | E | B | C | E |
| | 150 | B | B | B | E | E | E | D |
| | 75 | E | A | A | E | E | E | E |

TABLE VIII-continued

IN VIVO ACTIVITY OF MANCOZEB AND MANCOZEB + CuSO$_4$ (10%) AGAINST SELECTED FOLIAR PLANT PATHOGENS

| Compound | Conc. (ppm ai) | Disease Control Rating[1] | | | | | |
|---|---|---|---|---|---|---|---|
| | | BH[2] | RB | CA | BPM | GDM | TLB | WSR |
| | 38 | E | | E | E | E | E | E |

[1]Disease Control Rating:
A = 97-100%; B = 90-96%; C = 70-89%; D = 50-69% and E = <50%
[2]Diseases:
BH = Barley Net Blotch (*Helminthosporium teres*)
RB = Rice Blast (*Piricularia oryzae*)
CA = Cucumber Anthracnose (*Colletotrichum lagenarium*)
BPM = Bean Powdery Mildew (*Erysiphe polygoni*)
GDM = Grape Downy Mildew (*Plasmopora viticola*)
TLB = Tomato Late Blight (*Phytophthora infestans*)
WSR = Wheat Stem Rust (*Puccinia graminis triticia*)
[3]10% CuSO$_4$ is equivalent to 4% Cu (II) ion based on wt/wt mancozeb.

Table IX below demonstrates that the copper modified mancozeb products of the present invention are unexpectedly nonphytotoxic since it is known that copper fungicides are phytotoxic. In this test, the copper modified mancozeb products in the range of copper disclosed and claimed are not phytotoxic to tomato foliage.

TABLE IX

PERCENT FOLIAR INJURY

| Compound | | | Pounds of Product/ 100 gallons water | | | |
|---|---|---|---|---|---|---|
| | | | 2.0 | 4.0 | 8.0 | 16.0 |
| mancozeb | | | 0 | 1 | 10 | 15 |
| mancozeb | + | 10% CuSO$_4$ | 0 | 5 | 7 | 18 |
| mancozeb | + | 30% CuSO$_4$ | 0 | 8 | 17 | 63 |
| mancozeb | + | 60% CuSO$_4$ | 18 | 63 | 98 | 100 |
| mancozeb | + | 90% CuSO$_4$ | 33 | 98 | 100 | 100 |
| | | 100% CuSO$_4$ | 58 | 90 | 98 | 100 |

The copper modified mancozeb of the present invention can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual".

For the preparation of emulsifiable concentrates, the compound can be suspended in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of copper modified mancozeb, 45 parts of a synthetic precipitated hydrated silicon dioxide sold under the trademark Hi-Sil ®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex ®7.

Dusts are prepared by mixing the copper modified mancozeb with finely divided inert solids which can be organic or inorganic in nature. Materials useful for this purpose include botanical flours, silicas, silicates, carbonates, and clays. One convenient method of preparing a dust is to dilute a wettable powder with a finely divided carrier. Dust concentrate containing from about 20% to about 80% of the active ingredient are commonly made and are subsequently diluted to from about 1% to about 10% use concentration.

The copper modified mancozeb can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually from about 0.1 lbs to about 50 lbs. per acre of the active ingredient.

As a seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.1 to about 50 lbs. per acre. As a foliar fungicide, the toxicant is usually applied to growing plants at a rate of from about 0.25 to about 10 lbs. per acre.

Typical fungicides which can be combined with the fungicides of this invention includes:
  (a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine, diethyl phthalimidophosphorothioate, 4-butyl-1,2,4-triazole, 5-amino-1-[bis(dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,5-b]quinoxaline (thioquinox), methyl 1-(butylcarbamoyl)-2-benzimidazole carbamate (benomyl), 2-(4'-thiazolyl) benzimidazole (thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, α-(phenyl)-α-(2,4-dichlorophenyl)-5-pyrimidinyl-methanol (triarimol), cis-N-[(1,1,2,2-tetrachloroethyl)thio]-4-cyclohexene-1,2-dicarboxyimide, 3-[2-(3,5-dimethyl-2-oxycyclohexyl-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclododecyl-2,6-dimethylmorpholine (dodemorph), and 6-methyl-2-oxo-1,3-dithiolo[4,5-b]quinoxaline (quinomethionate).

(d) miscellaneous halogenated fungicides such as: tetrachloro-p-benzoquinone (chloranil), 2,3-dichloro-1,4-naphthoquinone (dichlone), 1,4-dichloro-2,5-dimethoxybenzene (chloroneb), 3,5,6-trichloro-o-anisic acid (tricamba), 2,4,5,6-tetrachloroisophthalonitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic copper carbonate, copper naphthenate, and Bordeaux mixture; and (g) miscellaneous fungicides such as: diphenyl, dodecylguanidine acetate (dodine), phenylmercuric acetate, N-ethylmercuri-1,2,3,6-tetrahydro-3,6-endomethano-3,4,5,6,7,7,-hexachlorophthalimide, phenylmercuric monoethanol ammonium lactate, p-dimethylaminobenzenediazo sodium sulfonate, methyl isothiocyanate, 1-thiocyano-2,4-dinitrobenzene, 1-phenylthiosemicarbazide, nickel-containing compounds, calcium cyanamide, lime sulfur, sulfur, and 1,2-bis(3-methoxycarbonyl-2-thioureido) benzene (thiophanatemethyl).

The copper modified mancozeb of this invention can be advantageously employed in various ways. Since this product possesses broad spectrum fungicidal activity, it can be employed in the storage of cereal grain. This product can also be employed as a fungicide in turf, fruit orchards, vegetables and golf course applications. Other applications of the copper modified mancozeb of this invention will suggest themselves to those skilled in the art of agriculture and horticulture.

I claim:

1. A copper modified mancozeb which comprises mancozeb reacted with from about 2.5% to about 20% copper (II) ion and a water solubilizing anion or complex thereof.

2. A copper modified mancozeb according to claim 1 wherein the copper (II) ion is from about 3% to about 10%.

3. A copper modified mancozeb according to claim 2 wherein the copper (II) ion is from about 4% to about 8%.

4. A copper modified mancozeb according to claim 1 wherein the water solubilizing anion is selected from the group consisting of halide, nitrate, perchlorate, sulfate, chlorate and bromate.

5. A process for preparing copper modified mancozeb which comprises reacting mancozeb with from about 2.5% to about 20% of copper (II) ion, in water in any order at temperatures from about 5° to about 90° C.

* * * * *